United States Patent
Keppler

(10) Patent No.: US 7,019,156 B2
(45) Date of Patent: Mar. 28, 2006

(54) TUMOR INHIBITING GALLIUM COMPOUNDS

(75) Inventor: Bernhard Keppler, Hockenheim (DE)

(73) Assignee: Faustus Forschungs Cie. Translational Cancer Research GmbH, Leipzig (DE)

( * ) Notice: Subject to any disclaimer, the term of this patent is extended or adjusted under 35 U.S.C. 154(b) by 0 days.

(21) Appl. No.: 10/678,292

(22) Filed: Oct. 3, 2003

(65) Prior Publication Data
US 2004/0110737 A1   Jun. 10, 2004

Related U.S. Application Data

(63) Continuation of application No. PCT/EP02/03560, filed on Mar. 28, 2002.

(30) Foreign Application Priority Data
Apr. 3, 2001   (DE) ................................. 101 16 527

(51) Int. Cl.
C07F 5/00 (2006.01)
A61K 31/555 (2006.01)
A01N 55/02 (2006.01)

(52) U.S. Cl. ........................... 556/35; 556/32; 514/188

(58) Field of Classification Search ................. 514/188; 556/32, 35
See application file for complete search history.

(56) References Cited

U.S. PATENT DOCUMENTS

| | | |
|---|---|---|
| 4,596,710 A | 6/1986 | Collery |
| 4,657,903 A | 4/1987 | Scovill et al. |
| 5,484,778 A | 1/1996 | Kenney et al. |
| 6,087,354 A | 7/2000 | Bernstein |

FOREIGN PATENT DOCUMENTS

| | | |
|---|---|---|
| EP | 0 525 938 | 2/1993 |
| WO | WO 9 302 087 | 2/1993 |

OTHER PUBLICATIONS

Carter, Stephen K., M.D. et al.; Chemotherapy of Cancer, Second Edition, (1981); A Wiley & Sons, New York, New York; pp 362-365.*

Klayman, D. L. et al.: "2-Acetylpyridine thiosemicarbazones. 6. 2-Acetylpyridine and 2-butyrylpyridine thiosemicarbazones as antileukemic agents" Arzneim.-Forsch. (1983), 33(7), 909-12, XP001071299 Zusammenfassung; S. 910, Verbindungen IV 2, VI 7, 17.

Hall, Iris H. et al.: "The cytotoxicity of heterocyclic thiosemicarbazones and their metal complexes on human and murine tissue culture cells" Anti-Cancer Drugs (1993), 4(2), 231-40, XP002079621 S. 232, Verbindung #4.

Kovala-Demertzi, Dimitra et al.: Palladium(II) complexes of 2-acetylpyridine N(4)-propyl-, N(4)- dipropyl- and 3-hexamethyleneiminylthiosemicarbazones with potentially interesting biological activity. Synthesis, spectral properties, antifungal and in vitro antitumor activity: POLYHEDRON (1997), 16(20), 3625-3633, XP002201201 S. 3626, Verbindung 7.

* cited by examiner

Primary Examiner—Sreeni Padmanabhan
Assistant Examiner—Gregory W Mitchell
(74) Attorney, Agent, or Firm—Michael Best & Friedrich LLP

(57) ABSTRACT

The invention relates to a compound of the general formula (I)

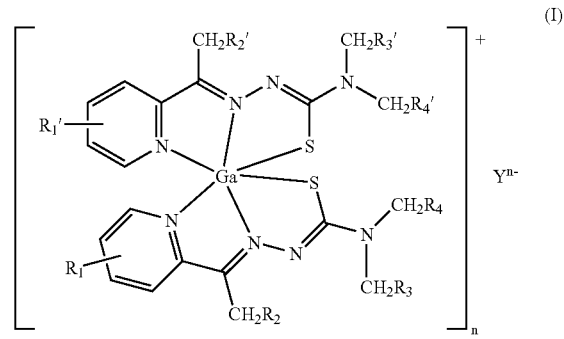

where
$R_1$, $R_2$, $R_3$, $R_4$, $R_1'$, $R_2'$, $R_3'$ and $R_4'$
are independently of one another hydrogen, $C_1$–$C_{15}$-alkyl, $C_2$–$C_{15}$-alkenyl, $C_2$–$C_{15}$-alkinyl, $C_3$–$C_{16}$-cycloalkyl, $C_3$–$C_{16}$-cycloalkenyl, aryl or a heterocyclus which in each case can be substituted or unsubstituted,
Y is a physiologically compatible anion, and
n is 1 or 2,
as well as its application to the prophylaxis and/or tretment of cancer illnesses.

20 Claims, No Drawings

TUMOR INHIBITING GALLIUM COMPOUNDS

CROSS-REFERENCE TO RELATED APPLICATIONS

This application is a continuation of and claims priority to International Application No. PCT/EP02/03560, filed on Mar. 28, 2002, which claims priority to German Application No. DE 101 16 527.7, filed on Apr. 3, 2001.

BACKGROUND OF THE INVENTION

In U.S. Pat. No. 6,087,354 pharmaceutical compositions are described which include gallium complexes of the 3-hydroxy-4-pyron. The compositions are suitable for many medical applications, such as the treatment of cancer illnesses.

U.S. Pat. No. 5,484,778 describes gallium phthalocyanine and its application in the treatment of cancer illnesses.

In U.S. Pat. No. 4,596,710 the application of gallium chloride in the treatment of malignant tumors is described.

EP-A-0525 938 describes gallium(III) complexes and their application in the treatment of hypercalcaemia and cancer illnesses.

Furthermore, in WO-A-9 302 087 the tumor-inhibiting effect of the complex compound tris(8-quinolinolato)-gallium(III) is described.

SUMMARY OF INVENTION

In one aspect, the invention provides a compound of the general formula (I)

[structure of formula (I) with gallium complex]

where
$R_1$, $R_2$, $R_3$, $R_4$, $R_1'$, $R_2'$, $R_3'$ and $R_4'$
are independently of one another hydrogen, $C_1$–$C_{15}$-alkyl, $C_2$–$C_{15}$-alkenyl, $C_2$–$C_{15}$-alkinyl, $C_3$–$C_{16}$-cycloalkyl, $C_3$–$C_{16}$-cycloalkenyl, aryl or a heterocyclus which in each case can be substituted or unsubstituted,
Y is a physiologically compatible anion, and
n is 1 or 2.

In another aspect, the invention may provide compounds which exhibit high effectiveness in the treatment of cancer illnesses.

DETAILED DESCRIPTION OF THE INVENTION

This invention relates to gallium compounds and their application as medication for the prophylaxis and/or treatment of cancer illnesses.

The invention provides compounds of the general formula (I)

[structure of formula (I) with gallium complex]

where
$R_1$, $R_2$, $R_3$, $R_4$, $R_1'$, $R_2'$, $R_3'$ and $R_4'$
are independently of one another hydrogen, $C_1$–$C_{15}$-alkyl, $C_2$–$C_{15}$-alkenyl, $C_2$–$C_{15}$-alkinyl, $C_3$–$C_{16}$-cycloalkyl, $C_3$–$C_{16}$-cycloalkenyl, aryl or a heterocyclus which in each case can be substituted or unsubstituted,
Y is a physiologically compatible anion, and
n is 1 or 2.

In one particular embodiment
$R_1$, $R_2$, $R_3$, $R_4$, $R_1'$, $R_2'$, $R_3'$ and $R_4'$
are independently of one another hydrogen, $C_1$–$C_{10}$-alkyl, $C_2$–$C_{10}$-alkenyl, $C_2$–$C_{10}$-alkinyl, $C_3$–$C_{10}$-cycloalkyl, $C_3$–$C_{10}$-cycloalkenyl, aryl or a heterocyclus which in each case can be substituted or unsubstituted and
Y is a metal halogen, halogeno-borate, halogen, pseudo-halogen, $HCO_3$ or R'COO, where R' is $C_1$–$C_{10}$-alkyl, $C_2$–$C_{10}$-alkenyl, $C_2$–$C_{10}$-alkinyl, $C_3$–$C_{10}$-cycloalkyl, $C_3$–$C_{10}$-cycloalkenyl or aryl, which can each be substituted or unsubstituted.

In another embodiment
$R_1$, $R_2$, $R_3$, $R_4$, $R_1'$, $R_2'$, $R_3'$ and $R_4'$
are independently of one another hydrogen, $C_1$–$C_6$-alkyl, $C_2$–$C_6$-alkenyl, $C_2$–$C_6$-alkinyl, $C_3$–$C_6$-cycloalkyl, $C_3$–$C_6$-cycloalkenyl, $C_6$–$C_{14}$-aryl or a heterocyclus which in each case can be substituted or unsubstituted and
Y is a metal halogen, halogen, pseudo-halogen, $HCO_3$ or R'COO, where R' is $C_1$–$C_6$-alkyl, $C_2$–$C_6$-alkenyl, $C_2$–$C_6$-alkinyl, $C_3$–$C_6$-cycloalkyl, $C_3$–$C_6$-cycloalkenyl or aryl, which can each be substituted or unsubstituted.

The halogen may be fluorine, chlorine, bromine or iodine, but fluorine, chlorine or bromine are preferred and especially chlorine.

The metal of the metal halogen may originate either from the main or secondary groups, but preferably from the 2nd, 3rd, 4th or 5th main group with special preference given to the 3rd main group and specially preferred is the metal gallium.

The halogen of the metal halogen is preferably defined for halogen as above.

In a preferred embodiment Y is in the general formula (I) a gallium halogen and particularly preferred is [$GaCl_4$].

The compounds according to the invention can be used for the prophylaxis and/or the treatment of cancer illnesses.

In the following the medicament containing the compound according to the invention is described in more detail.

The medicament according to the invention is primarily administered intravenously, but can also be administered by intramuscular means, intraperitonially, subcutaneously or perorally. An external application is also possible. Administering by intravenous injection or intravenous infusion is preferred.

The medicament is produced according to one of the known methods, whereby the compound according to the invention is used as it is or, where necessary, in combination with suitable pharmaceutical carrier materials. If the medicament according to the invention contains, apart from the active substance, pharmaceutical carrier materials, the content of active substance in this mixture is 0.1 to 99.5 and, more particularly, 0.5 to 95% by weight of the total mixture.

The medicament according to the invention can be used in any suitable formulation with the prerequisite that the formation or maintenance of sufficient levels of active substance is ensured. This can, for example, be achieved by oral or parenteral administering of suitable doses. Advantageously, the pharmaceutical preparation of the active substance is present in the form of individual doses which are matched to the required administered dosage. A standard dose may be, for example, a tablet, a dragée, a capsule, a suppository or a measured volume of a powder, granulate, solution, emulsion or a suspension.

A "standard dose" in the sense of this invention is taken to mean a physically determined unit which contains an individual quantity of the active constituent in combination with a pharmaceutical carrier substance and its content of active substance corresponds to a fraction or multiple of a therapeutic single dose. A single dose preferably contains the quantity of active substance which is administered during an application and which normally corresponds to a whole, half, third or quarter of the daily dose. If only a fraction, such as half or quarter of the single dose is needed for a single therapeutically administered dose, then the standard dose is advantageously divisible, e.g. in the form of a tablet with a dividing groove.

The medicaments according to the invention can, if they are available in standard doses and intended for application, e.g. on persons, contain about 0.1 to 500 mg, preferably 10 to 200 mg and particularly 50 to 150 mg of active substance.

Generally in human medicine, the active substance(s) are administered in a daily dose of 0.1 to 5, preferably 1 to 3 mg/kg of body weight, where necessary in the form of a number, preferably 1 to 3, of single intakes for achieving the desired results. A single intake contains the active substance (s) in quantities of 0.1 to 5, preferably 1 to 3 mg/kg of body weight. With oral treatment similar dosages can be applied.

The therapeutic administration of the medicaments according to the invention can occur 1 to 4 times daily at specified or varying time points, e.g. in each case before meals and/or in the evening. However, it may be necessary to deviate from the quoted dosages depending on the type, body weight and age of the individual to be treated, the type and severity of the illness, the type of preparation and the application of the medicament as well as the time period or interval within which the administration occurs. Consequently, in some cases it may be sufficient to use less than the amount of active substance mentioned above, whereas in other cases the above listed quantities of active substance must be exceeded. It may also be practicable to administer the medicaments only once or at intervals of several days.

The specification of the necessary optimum dosage and type of application of the active substances can be made by any specialist based on his specialist knowledge.

The medicaments according to the invention normally comprise the compounds according to the invention and non-toxic, pharmaceutically compatible medication carriers, which as additive or dilution agents, are employed, for example, in solid, semi-solid or liquid form or as a means of enclosure, for example in the form of a capsule, a tablet coating, a bag or another container for the therapeutically active constituent. A carrier material may, for example, act as an agent for the ingestion of the medicament by the body, as a formulation agent, sweetener, taste modifier, colorant or as preservative.

For oral application, for example, tablets, dragees, hard and soft capsules, for example of gelatine, dispersible powder, granulate, aqueous and oily suspensions, emulsions, solutions and syrups can be employed.

Tablets can contain inert dilution agents, e.g. calcium carbonate, calcium phosphate, sodium phosphate or lactose; granulation and distributing agents, e.g. maize starch or alginate; binding agents, e.g. starch, gelatine or arabine; and lubricating agents, e.g. aluminium or magnesium stearate, talcum or silicone oil. They can also be provided with a coating which is produced such that it causes delayed release and resorption of the medicament in the gastro-intestinal tract, so that, for example, improved compatibility, assimilation or retardation is achieved. Gelatine capsules may contain the pharmaceutical substance mixed with a solid, e.g. calcium carbonate or kaolin or an oily, e.g. olive, peanut or paraffin oil, dilution agent.

Aqueous suspensions can contain suspension agents, e.g. sodium carboxymethyl cellulose, methyl cellulose, hydroxypropyl cellulose, sodium alginate, polyvinyl pyrrolidon, traganth rubber or arabine; dispersant or wetting agents, e.g. polyoxyethylene stearate, heptadeca-ethylene-oxycatanol, polyoxyethylene sorbitol-monooleate, or lecithin; preservatives, e.g. methyl- or propylhydroxy-benzoate; taste modifiers; sweeteners, e.g. saccharose, lactose, sodium cyclamate, dextrose, invert sugar syrup.

Oily suspensions may be, for example, peanut, olive, sesame, coconut or paraffin oil and thickening agents, such as bees wax, high melting point wax or cetyl alcohol; also sweeteners, taste modifiers and antioxidants.

Powder and granulates dispersible in water may contain the compound according to the invention in a mixture with dispersing, wetting and suspension agents, e.g. those mentioned above as well as with sweeteners, taste modifiers and colorants.

Emulsions can, for example, contain olive, peanut or paraffin oil as well as emulsifying agents such as arabine, traganth rubber, phosphatides, sorbitan monooleate, polyoxyethylene sorbitan monooleate and sweeteners and taste modifiers.

Aqueous solutions can contain preservatives, e.g. methyl- or propylhydroxybenzoates, thickening agents; taste modifiers; sweeteners, e.g. saccharose, lactose, sodium cyclamate, dextrose, invert sugar syrup as well as taste modifiers and colorants.

For the parenteral application of the pharmaceutical substances sterile injectable aqueous solutions, isotonic salt solutions or other solutions can be used.

The following examples explain the invention.

EXAMPLE 1

Synthesis of bis(2-acetylpyridine-4,4-dimethyl thiosemicarbazonato-N1, N2,S)gallium(III) tetrachlorogallate(III)

Structure

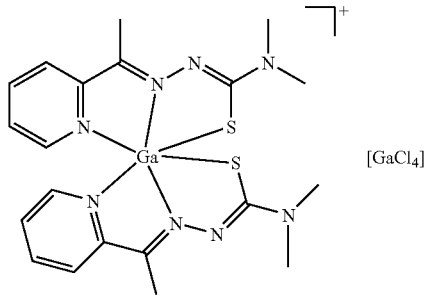

[GaCl$_4$]

Production occurs by the conversion of 2-acetylpyridine-4,4-dimethyl thiosemicarbazone (DATSC) with gallium(III) chloride (GaCl$_3$) in the ratio of DATSC: GaCl$_3$=1:1. In this process the ligand is dissolved at room temperature in absolute ethanol and then the (ethanolic) GaCl$_3$ solution added drop by drop within 5–10 minutes. The suspension of the precipitating product obtained under stirring is sucked off after one hour, washed with a little absolute ethanol and a large amount of absolute ether, recrystallised from absolute ethanol and dried in high vacuum.

Analysis:

| | |
|---|---|
| Calculated: | C: 33.19 H: 3.62 Cl: 19.60 N: 15.48 S: 8.86 Ga: 19.26 |
| Found: | C: 33.28 H: 3.67 Cl: 19.45 N: 15.22 S: 8.78 Ga: 19.60 |

EXAMPLE 2

Tumor-inhibiting Activity of bis(2-acetylpyridine-4,4-dimethyl thiosemicarbazonato-N1,N2,S)gallium (III) tetrachlorogallate(III)

Tests on two murine tumor cell lines under 96-hour exposition indicated an extraordinarily high tumor inhibiting activity (even in the nanomolar range):

MAC15A (murine adenocarcinoma of the colon):
IC$_{50}$: 0.11 nmol/l 0.08 ng/ml
F9 (murine teratocarcinoma of the testis):
IC$_{50}$: 17.4 nmol/l 12.6 ng/ml Furthermore, a very prominent selectivity was shown for mammary, prostate and macrocellular bronchial carcinomas (IC$_{50}$ <0.003 mg/ml). Comparable effects were also found on each of a stomach carcinoma and melanoma xenograft as well as on an ovarian (OVCAR3) and a parvicellular bronchial carcinoma cell line (DMS 114). An above-average activity was observed on one of two renal-cell carcinoma xenografts.

The invention claimed is:
1. A compound of the general formula (I)

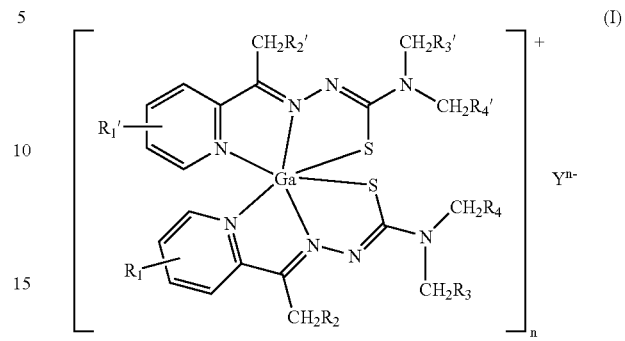

where
R$_1$, R$_2$, R$_3$, R$_4$, R$_1$', R$_2$', R$_3$' and R$_4$' are independently of one another hydrogen, C$_1$–C$_{15}$-alkyl, C$_2$–C$_{15}$-alkenyl, C$_2$–C$_{15}$-alkinyl, C$_3$–C$_{16}$-cycloalkyl, C$_3$–C$_{16}$-cycloalkenyl, aryl or a heterocyclus which in each case can be substituted or unsubstituted,
Y is a physiologically compatible anion, and
n is 1 or 2.

2. A compound according to claim 1, where Y is [GaCl$_4$].

3. A medicament containing a compound of the general formula (I) according to claim 1.

4. A medicament containing a compound of the general formula (I) according to claim 2.

5. A method of treatment of a cancer illness, the method comprising administering a compound of claim 1 to a living organism, wherein the cancer illness comprises at least one of adenocarcinoma of the colon, teratocarcinoma of the testis, mammary carcinoma, prostate carcinoma, macrocellular bronchial carcinoma, stomach carcinoma, melanoma xenograft, ovarian carcinoma and parvicellular bronchial carcinoma.

6. The method of claim 5, wherein the living organism is a human.

7. A method of treatment of a cancer illness, the method comprising administering a compound of claim 2 to a living organism.

8. The method of claim 7, wherein the living organism is a human.

9. A method of treatment of a cancer illness, the method comprising:
producing a medicament comprising a compound of claim 1; and
administering the medicament to a living organism,
wherein the cancer illness comprises at least one of adenocarcinoma of the colon, teratocarcinoma of the testis, mammary carcinoma, prostate carcinoma, macrocelullar bronchial carcinoma, stomach carcinoma, melanoma xenograft, ovarian carcinoma and parvicellular bronchial carcinoma.

10. The method of claim 9, wherein the living organism is a human.

11. A method of treatment of a cancer illness, the method comprising:
producing a medicament comprising a compound of claim 2; and
administering the medicament to a living organism.

12. The method of claim 11, wherein the living organism is a human.

13. The method of claim 5, wherein the cancer illness comprises adenocarcinoma of the colon.

14. The method of claim 5, wherein the cancer illness comprises teratocarcinoma of the testis.

15. The method of claim 5, wherein the cancer illness comprises at least one of mammary carcinoma, prostrate carcinoma and macrocellular bronchial carcinoma.

16. The method of claim 5, wherein the cancer illness comprises at least one of stomach carcinoma, melanoma xenograft, ovarian carcinoma and parvicellular bronchial carcinoma.

17. The method of claim 9, wherein the cancer illness comprises adenocarcinoma of the colon.

18. The method of claim 9, wherein the cancer illness comprises teratocarcinoma of the testis.

19. The method of claim 9, wherein the cancer illness comprises at least one of mammary carcinoma, prostrate carcinoma and macrocellular bronchial carcinoma.

20. The method of claim 9, wherein the cancer illness comprises at least one of stomach carcinoma, melanoma xenograft, ovarian carcinoma and parvicellular bronchial carcinoma.

* * * * *